United States Patent
Monneret et al.

(10) Patent No.: US 10,663,472 B2
(45) Date of Patent: *May 26, 2020

(54) METHOD FOR EVALUATING THE RISK OF MORTALITY IN PATIENTS WHO EXHIBIT A SYSTEMIC INFLAMMATORY RESPONSE SYNDROME (SIRS) OR SEPSIS

(71) Applicants: BIOMERIEUX, Marcy l'etoile (FR); HOSPICES CIVILS DE LYON, Lyons (FR)

(72) Inventors: Guillaume Monneret, Lyons (FR); Fabienne Venet, Lyons (FR); Alain Lepape, Saint-genis-laval (FR); Julie Demaret, Lyons (FR); Astrid Villars-Mechin, Lyons (FR)

(73) Assignees: BIOMERIEUX, Marcy l'Etoile (FR); HOSPICES CIVILS DE LYON, Lyons (FR)

(*) Notice: Subject to any disclaimer, the term of this patent is extended or adjusted under 35 U.S.C. 154(b) by 462 days.

This patent is subject to a terminal disclaimer.

(21) Appl. No.: 14/916,288

(22) PCT Filed: Sep. 18, 2014

(86) PCT No.: PCT/FR2014/052318
§ 371 (c)(1),
(2) Date: Mar. 3, 2016

(87) PCT Pub. No.: WO2015/040328
PCT Pub. Date: Mar. 26, 2015

(65) Prior Publication Data
US 2016/0195542 A1 Jul. 7, 2016

(30) Foreign Application Priority Data
Sep. 18, 2013 (FR) ...................... 13 58979

(51) Int. Cl.
*G01N 31/00* (2006.01)
*G01N 33/53* (2006.01)
*G01N 33/68* (2006.01)

(52) U.S. Cl.
CPC ..... *G01N 33/6869* (2013.01); *G01N 33/6893* (2013.01); *G01N 2333/70596* (2013.01); *G01N 2333/7155* (2013.01); *G01N 2800/24* (2013.01); *G01N 2800/26* (2013.01)

(58) Field of Classification Search
None
See application file for complete search history.

(56) References Cited

U.S. PATENT DOCUMENTS 9,823,239 B2 * 11/2017 Lepape ............... G01N 33/53
2015/0064728 A1 3/2015 Lepape et al.

FOREIGN PATENT DOCUMENTS

| FR | 2941240 A1 | 7/2010 |
| WO | 2010082004 A1 | 7/2010 |
| WO | 2012096245 A1 | 7/2012 |

OTHER PUBLICATIONS

Venet et al. (Critical Care, 2011, vol. 15, 231, pp. 1-9).*
Venet et al. (Critical Care, 2011, 15: 231, pp. 1-9).*
Boomer et al. (Critical Care, Jun. 2012, 16:R112, pp. 1-14).*
Crawley et al. (Journal of Immunology, 2010; vol. 184, pp. 4679-4687).*
Unsinger et al. (Journal of Immunology, 2010; vol. 184, pp. 3768-3779).*
Moreno et al. (Intensive Care Med. 2008, vol. 34, pp. 496-504).*
Venet et al. (Journal of Immunology, 2012; vol. 189, pp. 5073-5081).*
Venet et al. (Electronic Poster, Berlin 2011).*
Crawley et al. (J Immunology 2010; 184:4679-4687) (Year: 2010).*
A. Cheron, et al. :"Low monocytic HLA-DR expression and risk of secondary infection", Annales Francaises d'Anesthesie et de Reanimation 29(2010)368-376.
Caroline Landelle, et al. :"Low monocyte human leukocyte antigen-DR is independently associated with nosocomial infections after septic shock", Intensive Care Med (2010) 36:1859-1866.
Igor Kondrus, "Interactive superabsorbing bandage in complex treatment of purulent wounds in patients with disturbed blood flow due to artery deformity and collateral blood flow of neuroischemic form of diabetic food syndrome (DFS)".
Fabienne Venet, et al. :"Increased circulating regulatory T cells(CD4+ CD25+CD127−) contribute to lymphocyte anergy in septic shock patients", Intensive Care Med (2009) 35:678-686.
Thorsten Annecke, et al. :"Sevoflurane versus propofol in protection of the endothelial glycocalyx against ischemia-reperfusion injury", Inflamm. Res. (2010) 59 (Suppl 1): S9-S166.
Martin Sauer. "The extracorporeal immune support system (EISS) for the treatment of sepsis," Inflamm. Res.
Fabienne Venet, et al. :"Clinical review: flow cytometry perspectives in the ICU—from diagnosis of infection to monitoring of injury-induced immune dysfunctions", Venet et al. Critical Care 2011, 15:231.
Venet F. et al.:IL-7 restores lymphocyte functions in septic patients, J. Immunol., vol. 189, No. 10, Nov. 15, 2012, pp. 5073-5081.
Unsinger J. et al.: "IL-7 promotes T cell viability, trafficking, and functionality and improves survival in sepsis", J. Immunol., vol. 184, No. 7, Mar. 2010 (Mar. 2010), pp. 3768-3779, XP055100934.
Faucher S. et al.,:"Development of a quantitative bead capture assay for soluble IL-7 receptor alpha in human plasma", PLOS ONE, vol. 4, No. 8, E6690, Aug. 19, 2009, pp. 1-6.

(Continued)

*Primary Examiner* — Lisa V Cook
(74) *Attorney, Agent, or Firm* — Ladas & Parry LLP; Malcolm J. MacDonald (57) ABSTRACT

The invention provides a method of evaluating the risk of mortality in patients who present a systemic inflammatory response (SIRS) or septic syndromes, comprising measuring the expression of sCD127 in a biological sample.

3 Claims, 4 Drawing Sheets

(56) References Cited

OTHER PUBLICATIONS

Demaret J. et al.:Elevated plasmatic level of soluble IL-7 receptor is associated with increased morality in septic shock patients, Intensive Care Med., vol. 40, No. 8, Aug. 2014, pp. 1089-1096.
International Search Report dated Dec. 4, 2014, corresponding to International Patent Application PCT/FR2014/052318.

* cited by examiner

METHOD FOR EVALUATING THE RISK OF MORTALITY IN PATIENTS WHO EXHIBIT A SYSTEMIC INFLAMMATORY RESPONSE SYNDROME (SIRS) OR SEPSIS

This application is a 371 of PCT/FR2014/052318, filed on Sep. 18, 2014, which claims priority to French Application No. 1358979, filed Sep. 18, 2013.

The present invention relates to the medical field in general and in particular to the field of intensive care.

More precisely, the invention relates to a method of evaluating the risk of mortality in a patient who has been subjected to an insult such as surgery, burns, trauma, etc., generating a systemic inflammatory response syndrome, or SIRS, in a patient in a septic state, i.e. a patient presenting with SEPSIS, in particular severe SEPSIS, also known as serious SEPSIS, and preferably in a patient in septic shock.

Sepsis is a systemic inflammatory response syndrome related to an infection.

Severe sepsis is sepsis associated with arterial hypotension and/or hypoperfusion and/or dysfunction of at least one organ.

Septic shock is severe SEPSIS associated with persistent hypotension despite reasonable fluid resuscitation and vasopressor treatments.

The difference between SEPSIS, severe SEPSIS, and septic shock principally resides in the magnitude of the disruption to all of the vital functions.

SIRS patients presenting with septic syndromes, i.e. patients in a septic state as a result of SEPSIS, severe SEPSIS, or septic shock, represent one of the primary causes of mortality in intensive care units.

Estimating the risk of mortality in a SIRS, SEPSIS or severe SEPSIS patient and in particular in a patient in a state of septic shock, is thus essential in order to be able to provide personalized care and thus to attempt to reduce the risk of death.

The severity of the condition of a patient admitted into the intensive care unit is generally estimated with the aid of a variety of clinical and physiological parameters. They can in particular be used to define predictive scores in terms of survival/mortality; these include in particular SOFA (Sequential Organ Failure Assessment or Sepsis-related Organ Failure Assessment) and SAPSII (Simplified Acute Physiology Score II) (also IGS II (Indice de Gravité Simplifié II) [Simplified Gravity Index]) severity scores. These composite scores, defined through using substantial cohorts of intensive care patients, include a number of clinical-biological parameters such as the number of circulating platelets, bilirubinemia, diuresis, age, or body temperature. By calculating a numerical value, these scores can be used to evaluate the degree to which the function of one or more physiological systems (for example: cardiovascular, renal, cerebral) is under attack. They are calculated during the first days of admission to intensive care. In the case of the SAPSII score, only the worst value of the parameters included in the score, measured during the first 24 hours or their time in intensive care, is taken into consideration.

However, these scores are of little practical clinical use because they require the physician to carry out active investigation into the clinical parameters of a patient's history.

Thus, there is a genuine need for the provision of other tools, in particular measurable markers, that can be used to readily and rapidly evaluate the risk of mortality in a patient admitted into an intensive care unit, who by definition is in a serious condition that could become life-threatening. In fact, being able to identify subjects with an increased risk of mortality would mean that their care and follow-up and therapy could be made more suitable.

In this context, the present invention proposes providing a novel "biomarker" that can predict an increased risk of mortality in a patient who has been subjected to a severe insult (surgery, burns, trauma, etc.), generating a systemic inflammatory response (SIRS) or in a patient presenting with SEPSIS, in particular severe SEPSIS, and preferably in a patient in a state of septic shock. Studying the level of expression of this "biomarker" means that the risk of mortality of the patient can be evaluated readily and rapidly and all possible preventative measures can then be taken.

In a first aspect, the present invention therefore provides a method of evaluating the risk of mortality in a patient who has been subjected to an insult such as surgery, burns, trauma, etc., or to an infection generating a systemic inflammatory response or SIRS, the method comprising or even consisting of the following steps:

measuring the expression of sCD127 in a biological sample obtained from said patient, also known as the test sample; and     concluding whether there is an increased risk of mortality after comparing the expression of sCD127 with a reference value.

The method of the invention is a method that is carried out in vitro or ex vivo. It has the advantage of enabling the risk of mortality to be readily evaluated, in particular in a patient who has been admitted to an intensive care unit or as an emergency, by providing a marker that is directly measurable, in contrast to the SOFA and SAPSII severity scores, for example, and in which the measurement can be carried out in a laboratory that is nearby, or at the patient's bedside. The measurement of the marker is fully adapted to being carried out by automated analytical machines or by test methods known as rapid testing.

sCD127 is the soluble or plasmatic form of CD127, the IL-7 receptor. CD127, or the alpha chain of the IL-7 receptor, is a 75 kilodalton (kDa) glycoprotein that is a member of the hematopoietic growth factor receptor superfamily. It is expressed at the membrane in association with CD132 (common $Y_c$ chain) in order to form the IL-7 receptor. This receptor plays an important role in differentiation, survival and lymphocyte proliferation. CD127 is constituted by an extracellular 219 amino acid (aa) portion, a 25 aa transmembrane portion, and a 195 aa intracytoplasmic portion. The existence of a soluble/plasmatic form, denoted sCD127, generated by alternative splicing of the mRNA coding for CD127, is described in 1990 by Goodwin R G et al., Cell, 1990, 23, 941-951, but as yet its biological function is only poorly understood.

In the context of the invention, the term "sCD127" is used to mean the soluble or circulating form (also known as the plasmatic or seric form) of the IL-7 receptor, also known as the alpha chain of the IL-7 receptor or IL7R or IL7R-ALPHA or IL7RA or CDW127, and in particular as described by Goodwin et al, Cell, 1990, 23, 941-951 and assayed by Crawley et al, Journal of Immunology, 2010, 184, 4679-4687.

In particular, the reference nucleic sequences for CD127 and thus for sCD127 in accordance with the invention are preferably as follows: Ensembl: ENSG00000168685, HPRD-ID: 00893 and nucleotide sequence: NM_002185.2, VEGA genes: OTTHUMG00000090791.

Furthermore, the reference protein sequences for CD127 and thus for sCD127 in accordance with the invention are preferably as follows: NP_002176 XP_942460; version: NP_002176.2 GI:28610151.

The sample to be tested in the context of the method of the invention is a biological sample taken from a patient in whom the risk of mortality is to be evaluated. In particular, a biological sample of this type is selected from those that are susceptible of containing the marker sCD127.

In the context of the invention, the term "systemic inflammatory response" or "SIRS" is intended to mean a response associating at least two of the following criteria: temperature >38° C. or <36° C., heart rate >90 per minute (/min), respiratory rate >20/min or $paCO_2$<32 millimeters of mercury (mmHg), leukocytes >12000 per cubic millimeter (/mm$^3$) or <4000/mm$^3$ (Bone et al., Chest, 1992, 1644-1655.

The present invention presents a preferred application in patients presenting with SEPSIS, in particular severe SEPSIS. In particularly preferred manner, the method of the present invention is more particularly advantageous for evaluating the risk of mortality in a patient who is in a state of septic shock. In patients in a septic state (SEPSIS, severe SEPSIS, and septic shock) who present with SIRS following an infection, the infection may have a variety of origins, in particular a bacterial, viral, or fungal origin.

In a first preferred implementation, the method of the invention can be employed to conclude that there is an increased risk of mortality of a patient when an overexpression of sCD127 is demonstrated in the test sample compared with a first reference value.

The term "overexpression" means a significant increase in the level of expression relative to a reference value. The person skilled in the art is able to determine the statistical test to be used in order to determine the reference value with which the level of expression of sCD127 needs to be compared as a function of the comparison to be carried out, for example a comparison of populations or different types of samples, a comparison of the change over time of one population or of the same type of sample, etc., and to determine a significant increase in the level of expression of sCD127 as a function of the type of samples to be tested (for example plasma, serum, or blood), the type of immunological analysis carried out (for example blot, ELISA), or even the type of analytical equipment used, etc.

In this implementation, the first reference value may correspond to the level of expression of sCD127 measured in a biological sample obtained from a patient who has been subjected to an insult or to an infection generating a systemic inflammatory response which that patient is known to have survived, in particular a patient presenting with SEPSIS which that patient is known to have survived, and preferably a patient in septic shock which that patient is known to have survived.

In this situation, the measurement of the expression of sCD127 that constitutes the first reference value is preferably carried out in parallel, i.e. at the same time as the measurement of the expression of sCD127 that is carried out on the sample obtained from the patient in whom the risk of mortality is to be evaluated, even though the reference sample would have been taken at a time that was earlier than the time of taking the test sample.

This first reference value may also correspond to a mean value for the level of expression of sCD127 that is measured on a pool of samples obtained from patients who have been subjected to an insult such as surgery, burns, trauma, etc., or to an infection generating a systemic inflammatory response (SIRS) that those patients are known to have survived, in particular patients presenting with SEPSIS that those patients are known to have survived, preferably patients in a state of septic shock that those patients are known to have survived. In this situation, the measurement of the expression of sCD127 that constitutes the first reference value is preferably carried out prior to measuring the expression of sCD127 that is carried out on the sample obtained from the patient in whom the risk of mortality is to be evaluated, even though reference samples that are to be "pooled" will have been taken at a time that was earlier than the time of taking the test sample.

In this first preferred implementation, and in particular in order to evaluate the risk of mortality of a patient in a state of septic shock, the measurement of the expression of sCD127 in the test sample and, where appropriate, in the biological sample used to obtain the first reference value is carried out within 4 days, or on day 4 (D4) after the septic shock, preferably within 3 days, or on day 3 (D3) after the septic shock, more preferably within 2 days, or on day 2 (D2) after the septic shock, and particularly preferably within the day, or on day 1 (D1) after the septic shock. In other words, this first reference value is produced within 4 days, within 3 days, within 2 days, within the day after the septic shock or on day 4, on day 3, on day 2, on day 1 after the septic shock. In accordance with a particularly advantageous implementation of this first implementation of the invention, the first reference value is produced within 2 days or within the day, or indeed on day 2 or on day 1 after the septic shock, which means that the risk of the mortality of the tested patient can be determined very early on.

In accordance with a second preferred implementation, the method of the invention can be used to conclude that there is an increased risk of mortality in a patient when the expression of sCD127 that is measured in the test sample is not significantly reduced compared with a second reference value. The person skilled in the art is capable of determining the significant percentage reduction, which depends on the type of test sample (for example plasma, serum or blood), or the type of immunological analysis (for example blot, ELISA), or indeed on the equipment on which the analysis is made, etc. In general, an increased risk of mortality is concluded if the expression of sCD127 that is measured in the test sample has not been reduced by more than 30% compared with this second reference value, and preferably has not been reduced by more than 25%, and in particular has not been reduced by more than 20%, or indeed has not been reduced by more than 15% or than 10% compared with this second reference value.

This second reference value may correspond to the level of expression of sCD127 measured in a biological sample obtained from the same said patient when sampled previously, i.e. in a biological sample obtained from the patient in whom the risk of mortality is to be evaluated and obtained at a time earlier than the time of the test sample. The term "earlier" or "prior" is used to mean earlier in time. Preferably, the second reference value corresponds to the level of expression of sCD127 as measured in a biological sample that was immediately prior to the test sample i.e. that preceded the test sample in the order of samples taken from the patient.

In this second preferred implementation, and in particular in order to evaluate the risk of mortality of a patient in a state of septic shock, the expression of sCD127 in the test sample is measured at or about 7 days (D7) after the septic shock, more preferably at or about 4 days after the septic shock, in particular about 3 days or 3 days after the septic shock, and still more preferably about 2 days or 2 days after the septic shock.

By way of example, the earlier sample may be taken within 48 hours (h) or 48 h after the septic shock and at least 24 h before that of the test sample, and preferably the earlier sample is taken within 48 h or 48 h after the septic shock and the test sample is taken within the 48 h that follow taking the earlier sample or 48 h after taking the earlier sample.

Thus, in all situations, before measuring the expression of sCD127 proper in the test sample, the method of the invention may comprise obtaining the reference value at an earlier time for comparison with the level of expression that is to be detected in the test sample, regardless of whether this is the first reference value or the second reference value, in order to conclude that there is or is not an increased risk of mortality in the patient from whom the test sample has been taken.

Thus, it is with these reference values, regardless of whether they are the first reference value or the second reference value, as obtained previously or at the same time, that are to be compared with the value for the expression of sCD127 as measured in the test sample.

The sample on which the method of the invention is carried out, also termed the test sample, may be of animal or human origin, preferably of human origin.

The test sample may be a biological fluid, for example selected from blood, whole blood in particular taken from a vein, i.e. containing white and red cells, platelets and plasma, serum, plasma, and bronchoalveolar lavage fluid.

Preferably, the test sample obtained from said patient is a sample of plasma or serum.

The samples from which the reference values may be determined, regardless of whether they pertain to the first reference value or the second reference value, also known as the "reference samples", may be of different natures and in particular of a biological nature as mentioned above in respect of the test sample (biological fluids). Advantageously, these biological samples are of the same nature as that of the biological sample to be tested, or at least of a nature that is compatible with constituting a reference as regards detection and/or quantification of the expression of sCD127.

In order to obtain the first reference value in particular, these samples are preferably obtained from individuals having the same characteristics or a majority of common characteristics, in particular the same sex and/or similar or identical age and/or the same ethnic origin, as those of the subject or patient in whom the risk of mortality is to be evaluated. In this case the reference sample may also be constituted by any, biological or non-biological sample that has been calibrated to contain a mean value of sCD127 that corresponds to the level as measured for a pool of biological samples obtained from patients who have been subjected to an insult such as surgery, burns, trauma, etc., or to an infection generating a systemic inflammatory response (SIRS) that those patients are known to have survived, in particular patients presenting with SEPSIS that they are known to have survived, and preferably patients in a state of septic shock that they are known to have survived. In this situation, and in a particularly preferred variation, the reference sample is obtained from one or more patients in a state of septic shock which that/those patient/s is/are known to have survived.

In order to obtain the second reference value in particular, the reference sample is preferably a biological sample obtained from a patient in whom the risk of mortality is to be evaluated and from whom the test sample has been obtained, but obtained from a sample taken at a time earlier than the time of the test sample. Preferably, the second reference value is obtained from a biological sample that was taken at a time immediately prior to the time of the test sample, i.e. the sample preceding the test sample in the order in which the samples are taken from the patient.

In a particular implementation, the method of the invention comprises measuring the expression of sCD127 combined with estimating at least one of the SOFA and/or SAPSII severity scores in order to evaluate the risk of mortality of the patient who has been subjected to an insult or to an infection generating a systemic inflammatory response (SIRS), and in particular from a patient who is in a state of septic shock. In this implementation, the SOFA score is preferably calculated as described by D. L. Vincent et al., *Intensive Care Med.*, 1996; 22:707-710, and/or the SAPSII score is preferably calculated as described by D. R. Le Gall et al., *JAMA*, 1993; 270:2957-63.

In the context of the present invention, the term "measure the expression" is intended to mean an in vitro or ex vivo measurement. Furthermore, this term is intended to designate the detection and quantification of sCD127, preferably at the protein level.

In this regard, any method of detection and/or quantification that is familiar to the person skilled in the art may be used to implement the invention, regardless of whether it is in relation to determining the presence of and/or measuring the expression of the sCD127 protein. By way of an example of the method of measuring the expression of the sCD127 protein, reference may in particular be made to that described by Crawley et al, *Journal of Immunology*, 2010, 184, 4679-4687.

In particular, the level of expression of sCD127 is measured with the aid of tools or reagents that are specific to sCD127 that can be used directly or indirectly to determine its presence and/or to quantify its level of expression.

Examples of tools or reagents that are capable of detecting and/or quantifying sCD127 and that may be mentioned are specific antibodies, which may be polyclonal or monoclonal, preferably monoclonal, or fragments or derivatives thereof, for example Fab, F(ab)'2, Sv, scFv fragments, or antibody analogs, in particular affinity proteins with competitive properties (Nanofitins™).

Preferred examples of these tools or reagents are those that are specific for the soluble form of the IL-7 receptor, i.e. that do not recognize CD127, which is the insoluble cellular/membrane form of this receptor. However, tools or reagents that recognize both the soluble form, or sCD127, and the cellular form of the IL-7 receptor, or CD127, may be used as long as it is possible to distinguish these two forms by some other means, such as the nature of the sample being analyzed (for example plasma or serum versus biological sample containing cells or whole blood).

When the sCD127 is detected and/or quantified on a protein level, standard techniques such as Western blot, ELISA, RIA, IRMA, FIA, CLIA, ECL, flow cytometry or immunocytology may be used.

Particularly advantageously, the expression of sCD127 is measured on a protein level, and preferably with the aid of an ELISA technique.

In the invention, and in particular in this particular implementation, the level of expression of sCD127 is preferably measured with the aid of an anti-sCD127 antibody, which may be monoclonal or polyclonal, and in particular anti-sCD127 monoclonal antibody. By way of example, R34.34 anti-human CD127 monoclonal antibodies sold by Beckman Coulter® or anti-CD127 polyclonal antibodies sold by R&D Systems® may be used.

All of the indications and preferences mentioned above concerning the measurement of the expression of sCD127 are equally applicable to the measurement of this expression in the test sample and in the reference sample.

In a second aspect, the present invention also provides the use of the measurement, in vitro or ex vivo, of the expression of sCD127 in order to evaluate the risk of mortality in a patient who has been subjected to an insult such as surgery, burns, trauma, etc., or to an infection generating a systemic inflammatory response or SIRS, in particular a patient presenting with SEPSIS, in particular severe SEPSIS.

Preferably, this use is particularly advantageous for evaluating the risk of mortality in a patient who is in septic shock.

Furthermore, in the context of the use of the invention, the expression of sCD127 is preferably measured at the protein level and in particular with the aid of an ELISA technique.

In particular, the expression of sCD127 may be measured using a monoclonal or polyclonal anti-sCD127 antibody, preferably a monoclonal anti-sCD127 antibody. The antibodies mentioned above may also be used in this second aspect of the invention.

In a broader aspect, all of the preferred implementations mentioned above concerning the method and their combinations also constitute preferred implementations as regards the use. More particularly, the use in accordance with the invention may in particular comprise measuring the expression of sCD127 combined with an estimate of at least one of the SOFA and/or SAPSII severity scores in order to evaluate the risk of mortality in a patient who has been subjected to an insult or to an infection generating a systemic inflammatory response (SIRS), and in particular in a patient who is in a state of septic shock.

In a third aspect, the present invention also provides a kit for in vitro or ex vivo measurement of the expression of sCD127 in a biological sample, comprising:
  specific tools or reagents for measuring the expression of sCD127 in said biological sample; and
  a positive control sample, which is a sample calibrated to contain the quantity of sCD127 that corresponds to the mean quantity measured in a pool of samples from patients who are known to have survived, and/or a negative control sample, which is a sample calibrated to contain the quantity of sCD127 that corresponds to the mean quantity measured in a pool of samples from patients who are known not to have survived.

Thus, the kit in accordance with the invention comprises specific tools or reagents for measuring the expression of sCD127 in said biological sample, and at least one control sample.

In particular, the kit of the invention can be used to evaluate the risk of mortality in a hospitalized patient who has been the subject of an insult such as surgery, burns, trauma, etc., or to an infection generating a systemic inflammatory response (SIRS), and in particular in a patient who is in a state of septic shock.

Preferably, the specific tools or reagents that can be used to measure the expression of sCD127 in a biological sample that are present in the kit of the invention can be used to detect and/or quantify the expression of sCD127, and preferably at the protein level.

In a particularly preferred embodiment, the kit of the invention contains monoclonal or polyclonal anti-sCD127 antibodies, in particular monoclonal antibodies, as specific tools or reagents enabling the expression of sCD127 in said biological sample to be measured.

Another positive control sample may also be a biological sample obtained from at least one patient who is known to have survived. Similarly, another negative control sample may also be a biological sample obtained from at least one patient who is known not to have survived. Regardless of whether it is for a positive or negative control, this type of control sample is in particular obtained from one or more patient(s) who have been subjected to an insult such as surgery, burns, trauma, etc., or to an infection generating a systemic inflammatory response (SIRS), in particular one or more patient(s) presenting with SEPSIS, and preferably one or more patient(s) in a state of septic shock.

Preferably, the kit comprises both a positive control sample and a negative control sample, and in particular each selected from calibrated samples as defined above.

The invention also encompasses the use of a kit of the invention for carrying out the method of the invention, and in particular to evaluate the risk of mortality in a patient who has been subjected to an insult such as surgery, burns, trauma, etc., or to an infection generating a systemic inflammatory response (SIRS), in particular in a patient presenting with SEPSIS, in particular severe SEPSIS. Preferably, using the kit of the invention enables the risk of mortality in a patient who is in a state of septic shock to be evaluated.

All of the preferred implementations that are mentioned above concerning the method and their combinations also constitute preferred embodiments of the kit of the invention and its use.

Various other characteristics become apparent from the description below made with reference to the accompanying figures which, by way of non-limiting examples, show implementations of the subject matter of the invention, in which.

METHODS

Biological Samples

Plasma samples were taken from 70 patients in septic shock on days 1-2 (D1-2) and 3-4 (D3-4) after septic shock, and were then stored (retrospective cohort). Plasma samples were also taken from 41 healthy volunteer subjects.

28 days after admission to intensive care for septic shock, 14 patients had not survived ("NS") i.e. 20%, while 56 patients ("S") out of the 70 patients had survived.

Assay of the Soluble Form of the IL-7 Receptor (sCD127) by ELISA

"Coating"

A "coating" buffer was prepared containing 0.8 grams (g) $Na_2CO_3$, 1.4 g $NaHCO_3$ and 0.1 g $NaN_3$ in 500 millimeters (mL) of water (pH 9.6).

100 µL of capture antibody (Ab) (mouse anti-human CD127 monoclonal antibody R34.34, Beckman Coulter®) diluted in a "coating" buffer were deposited per well in a plate ([Ab]=8 µg/mL). The plate was then covered and incubated at 4° C. overnight.

The contents of the well were then aspirated and the wells were washed 3 times with at least 300 µL of 0.05% PBS-TWEEN20® non-ionic detergent washing buffer. All of the liquid was carefully removed at each wash. After the last wash, the plate was turned upside down on adsorbent paper in order to eliminate all traces of buffer.

"Blocking"

Non-specific fixing was blocked with the aid of 150 µL of blocking buffer per well (10% fetal calf serum (FCS)/PBS-TWEEN20® non-ionic detergent, 0.05%), then the plate was incubated for 1 h at 37° C.

Again, the contents of the well were aspirated and the wells were washed 3 times with at least 300 µL of 0.05% PBS-TWEEN20® non-ionic detergent washing buffer. All of the liquid was carefully removed at each wash. After the last wash, the plate was turned upside down on adsorbent paper in order to eliminate all traces of buffer.

Samples and Controls

A calibration scale was produced with recombinant human IL-7Rα/CD127 Fc chimera (R&D Systems—Catalog number: 306-IR) diluted in PBS 5% FCS dilution buffer, as described in Table 1 below and in accordance with C. Janot-Sardet et al. *Journal of Immunological Methods*, 2010, 28, 115-123.

TABLE 1

| | rh IL-7Rα/CD127 Fc chimera | | | | | | | |
|---|---|---|---|---|---|---|---|---|
| [c] (ng/mL) | 500 | 250 | 125 | 62.5 | 31.25 | 15.7 | 7.85 | 0 |
| Diluent (µL) | 0 | 100 | 100 | 100 | 100 | 100 | 100 | 100 |
| Solution, 500 ng/mL (µL) | 100 | 100 | | Successive dilutions | | | | 0 |

100 µL of sample or control (solution of CD127 Fc chimera reconstituted extemporaneously and in aliquots at concentrations of 60 ng/mL and 10 ng/mL) were added to each well, then the plate was incubated for 1 h at 37° C.

Again, the contents of the well were aspirated and the wells were washed 3 times with at least 300 µL of 0.05% PBS-TWEEN20® non-ionic detergent washing buffer. All of the liquid was carefully removed at each wash. After the last wash, the plate was turned upside down on adsorbent paper in order to eliminate all traces of buffer.

Detection Antibody

100 µL of detection antibody (biotinylated goat polyclonal anti-CD127 antibody reconstituted with 1 mL of 1% TBS-BSA, R&D Systems®) diluted in PBS/5% FCS was added to each well ([Ab]=200 ng/mL), then the plate was incubated for 1 h at 37° C.

Again, the contents of the well were aspirated and the wells were washed 3 times with at least 300 µL of 0.05% PBS-TWEEN20® non-ionic detergent buffer. All of the liquid was carefully removed at each wash. After the last wash, the plate was turned upside down on adsorbent paper in order to eliminate all traces of buffer.

Revealing

100 µL of Streptavidin-HRP was added to each well ([Streptavidin-HRP]=8 µL/mL). The plate was then covered and incubated for 30 min at ambient temperature.

Again, the contents of the well were aspirated and the wells were washed 3 times with at least 300 µL of 0.05% PBS-TWEEN20® non-ionic detergent washing buffer. All of the liquid was carefully removed at each wash. After the last wash, the plate was turned upside down on adsorbent paper in order to eliminate all traces of buffer. At this washing stage, the wells were soaked with washing buffer for 1 min to 2 min before aspiration.

The two flasks of the colorimetric substrate TMB (3,3', 5,5'-tetramethylbenzidine, bioMérieux # XX7LF1UC) were mixed volume to volume and 100 µL of this substrate solution was deposited into each well. The plate was then covered and incubated for 30 min at ambient temperature.

Finally, the plate was read by measuring the absorbance at 450 nm.

Multivariate Analysis

A Cox model allowed the "Hazard Ratio" and its 95% confidence interval (95% CI) along with its significance to be estimated. The SAPSII and SOFA scores were included in the model in the form of continuous variables, assuming a linear relationship between their values and the risk of death (survivors vs non-survivors). The statistical analyses were carried out using SPSS (version 17.0, SPSS, Chicago, Ill.) and GraphPad Prism (version 5.03, GraphPad Software, La Jolla, Calif.) software. Values for p of less than 0.05 were considered to be significant.

Survival Comparison Analysis ("Log Rank" Test)

The ROC (Receiver Operating Characteristic) curves were generated using the software mentioned above and the optimized concentration or optimum sCD127 threshold for obtaining the best sensitivities and specificities was defined by means of a Youden's index, which combines the parameters of sensitivity and specificity for incremental values for the marker under consideration. The optimized concentration of the marker that provides the highest Youden's index, i.e. an optimized sensitivity and specificity, was thus determined. The Kaplan-Meier survival curves were obtained after stratification of the patients on the basis of this optimized value. The difference in survival between the groups was evaluated using the "Log Rank" test and the "Hazard Ratio" (and its confidence interval of 95%), calculated on the basis of the slopes of these survival curves.

Results

Assay of the Soluble Form of the IL-7 Receptor (sCD127)

The concentration of plasmatic sCD127 was measured as described above in plasma samples from 70 patients in septic shock and the SOFA and SAPSII severity scores were evaluated in these patients on the basis of the clinical and physiological data available for the first 24 hours of hospitalization.

The same measurements were also carried out on samples obtained from 41 healthy volunteer subjects (HV).

The results are summarized in Tables 2 to 4 below:

Capacity of sCD127 to Predict the Death of Patients in Septic Shock

The predictive capacity of the measurement of the concentration of plasmatic sCD127 was studied having regard to the event to be studied, namely mortality. That from two reference scores, SAPSII and SOFA, was also studied in respect of this same event.

Figure 1:
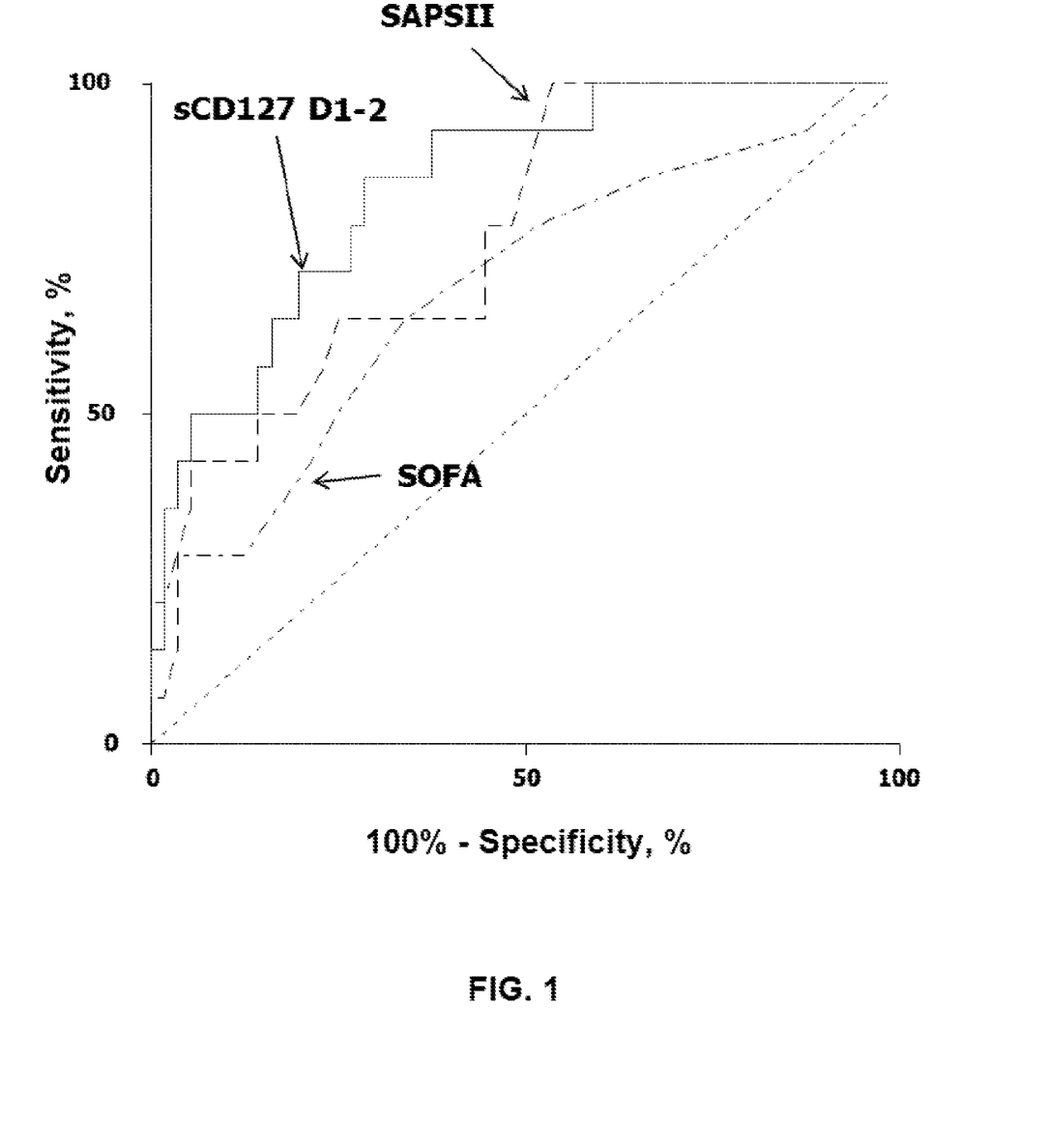
FIG. 1 shows the ROC curve of the concentration of plasmatic sCD127 measured on D1-2, the SAPSII score and the SOFA score in 70 patients after septic shock.

The results are represented in FIG. 1 in the form of a ROC (Receiving Operating Characteristic) curve for sCD127 measured on D1-2 and the SAPSII and SOFA severity scores in 70 patients with septic shock.

The evaluation of the areas under the curve, reported in Table 2 below, mean that the predictive performances of the known SOFA and SAPSII scores can be compared with that of the measurement of plasmatic sCD127.

TABLE 2

|  | Area under the curve (AUC) | Value of p |
|---|---|---|
| sCD127 measured on D1-2 | 0.846 | P < 0.001 |
| sCD127 measured on D3-4 | 0.774 | P = 0.002 |
| SOFA on D1 | 0.692 | P = 0.027 |
| SAPSII on D1 | 0.770 | P = 0.002 |

For the values of sCD127 measured on D1-2, the optimum threshold was defined as 44.45 ng/mL using Youden's index, which provided a sensitivity of 86%; a specificity of 71%, a positive predictive value (probability that the patient will die if the test is above the threshold) of 43% and a negative predictive value (probability that the patient will survive when the test is below this threshold) of 95%.

Similarly, for the values of sCD127 measured at D3-4, the optimum threshold was defined as 48.10 ng/mL, which provided a sensitivity of 71%; a specificity of 86%, a positive predictive value of 56% and a negative predictive value of 92%.

By comparison, with the SOFA score measured at D1, the sensitivity was 64.3% and the specificity was 66.1%, with a positive predictive value of 32.1% and a negative predictive value of 88.1%.

With the SAPSII scored measured at D1, the sensitivity was 71.4% and the specificity was 55.4%, with a positive predictive value of 28.6% and a negative predictive value of 88.6%.

Thus, these results show that the measurement at D1-2 of the concentration of sCD127 in plasma from patients has a better capacity for predicting post-septic shock death than the conventionally used SOFA and SAPSII scores (based on the areas under the ROC curves).

Multivariate Analysis

In order to evaluate the independence of the link between the plasma concentration of sCD127 and the risk of death compared with known risk factors for patients in septic shock (initial severity and number of failed organs evaluated by the SAPSII and SOFA scores), uni- and multivariate logistical regression analyses were carried out as described above.

A multivariate analysis between the SOFA, SAPSII scores and the measurement of sCD127 obtained at D1-2 and D3-4 was carried out. The results, which are summarized in Tables 3 and 4 below, show that the measurement of sCD127 is a marker that is entirely independent of the two known risk factors, SOFA and SAPSII for the prediction of post-septic shock mortality.

TABLE 3

|  | Value of p | "Hazard Ratio" | 95% confidence interval |
|---|---|---|---|
| sCD127 D1-2 | 0.004 | 8.153 | 1.927-34.503 |
| SOFA | 0.872 | 1.125 | 0.268-4.718 |
| SAPSII | 0.062 | 3.887 | 0.936-16.149 |

TABLE 4

|  | Value of p | "Hazard Ratio" | 95% confidence interval |
|---|---|---|---|
| sCD127 D3-4 | 0.011 | 6.748 | 1.55-29.374 |
| SOFA | 0.599 | 1.436 | 0.373-5.526 |
| SAPSII | 0.06 | 3.787 | 0.947-15.141 |

Kaplan-Meier Survival Curves

Figure 2A:
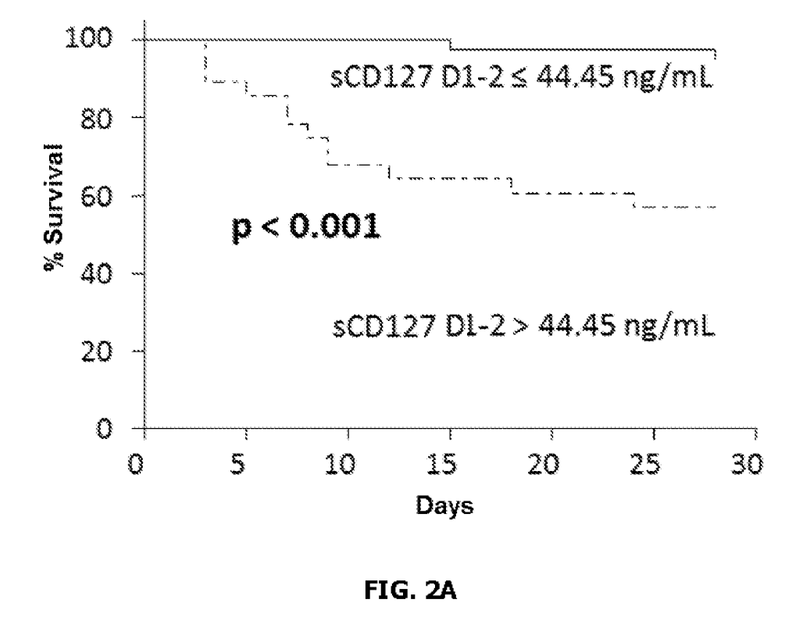
FIGS. 2A, 2B and 2C show the survival curves for sCD127 for 70 patients at D1-2 (A) and D3-4 (B) and the SAPSII score (C) after septic shock.
Figure 2B:
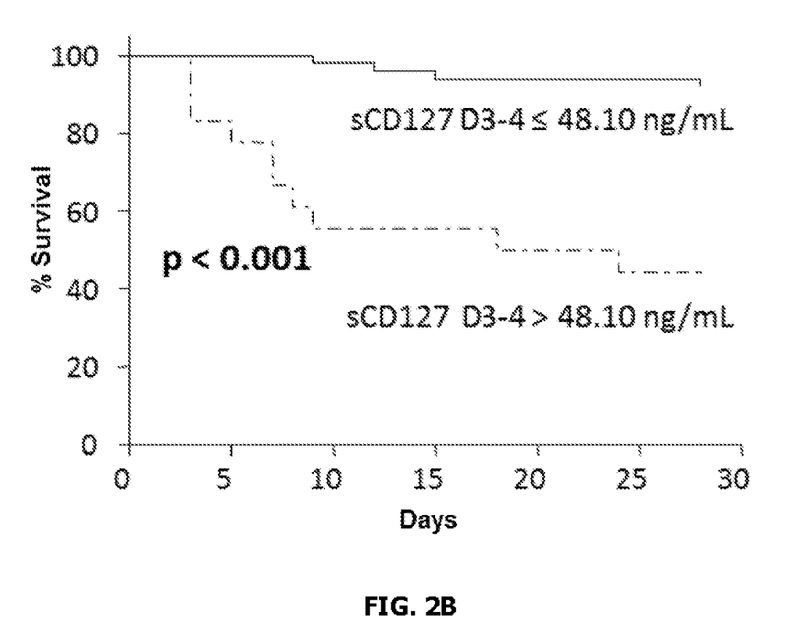

Survival curves were established on the basis of optimum threshold values determined using the ROC curves and Youden's index for sCD127 at D1-2 and D3-4. The survival curve after stratification of patients on the basis of the SAPSII score was also generated (threshold equal to 53). The results are shown in FIGS. 2A, 2B, and 2C.

Regardless of whether it was at D1-2 (FIG. 2A) or at D3-4 (FIG. 2B), these results show a significant difference between the two survival curves traced as a function of the optimum threshold of sCD127 (D1-2 (FIG. 2A): "Hazard ratio"=10.22; [95% CI]: 3.36-31.13; p<0.001, "Log Rank" test; D3-4 (FIG. 2B): "Hazard ratio"=28.50; [95% CI]: 7.519-108.0); p<0.001, "Log rank" test.

Figure 2C:
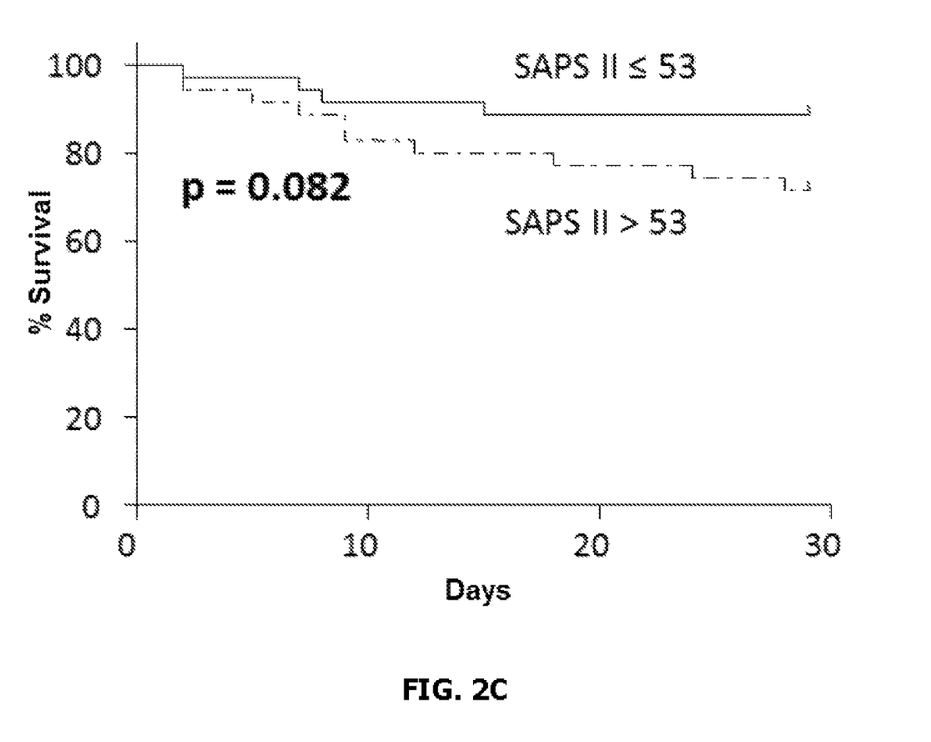

In contrast, after stratification on the basis of the SAPSII score, no significant difference in mortality was demonstrated (FIG. 2C: p=0.082, "Log Rank" test, "Hazard ratio"=2.55, [95% CI]: 0.887-7.309).

Figure 3A:
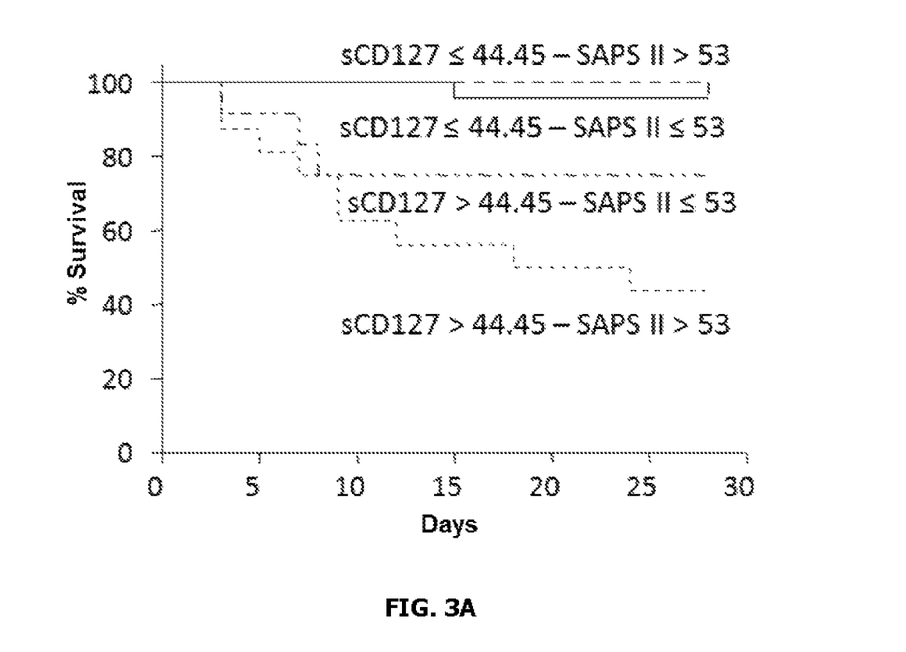
FIGS. 3A and 3B show the survival curves for the combination of sCD127 for 70 patients at D1-2 (A) and D3-4 (B) after septic shock and the SAPSII score.
Figure 3B:
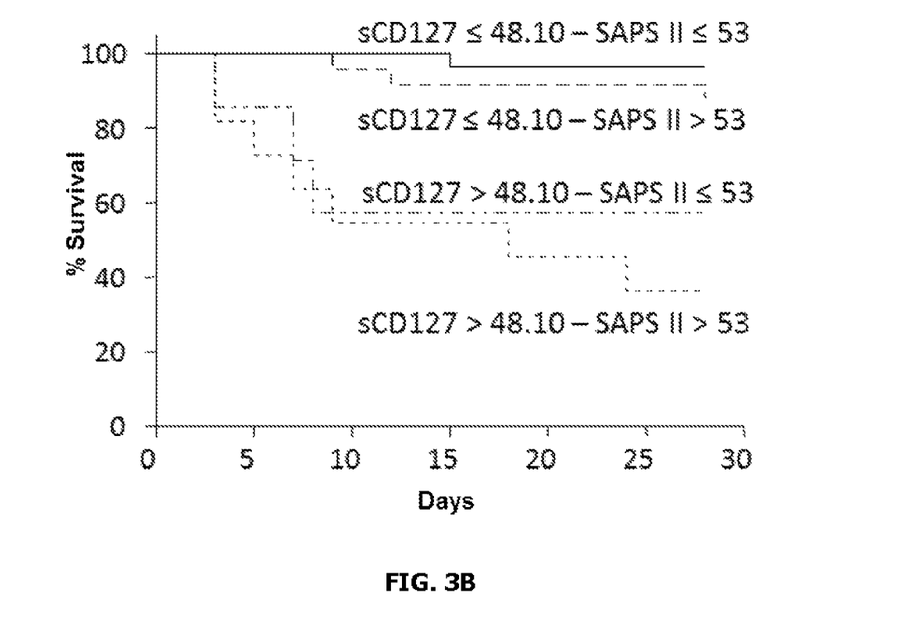

Finally, the predictive capacity of the risk of death of the combination of an augmented value of sCD127 and an augmented SAPSII score was evaluated as described above, after stratification of the patients on the basis of optimum threshold values determined using ROC curves and Youden's index for sCD127 at D1-2 and at D3-4 and the optimum threshold for SAPSII (threshold equal to 53). The corresponding survival curves were thus also generated, and the results are represented in FIGS. 3A and 3B respectively.

Regardless of whether it was at D1-2 or at D3-4, these results show that the patients who have the lowest concentrations of sCD127 and the lowest SAPSII score have a much better chance of survival, compared with those who have higher concentrations of sCD127 and the highest SAPSII score:

D1-2 (FIG. 3A): p<0.001, Log Rank test, Hazard ratio=12.98; [95% CI]: 3.453-48.83.

D3-4 (FIG. 3B): p<0.001, Log Rank test, Hazard ratio=50.94; [95% CI]: 9.352-277.4).

These results demonstrate that the combined measurement of sCD127 and at least one of the SAPSII or SOFA scores can augment the strength of predictions of mortality in patients who are hospitalized in intensive care.

As a consequence, this series of results demonstrate that measuring the expression of sCD127 in plasma is a very useful and reliable immunological marker for evaluating the risk of mortality in a patient admitted into an intensive care unit, and in particular a patient in a state of septic shock. In addition, this parameter can be combined with the usual clinical scores in order to improve the predictive capacity of the risk of death for these scores.

The invention is not limited to the examples described and represented, since a variety of modifications may be provided thereto without departing from the scope of the invention.

The invention claimed is:

1. A method of evaluating a risk of mortality in a patient in a state of septic shock, the method comprising:
  measuring a level of expression of soluble CD127 in a test sample that is a biological sample taken from the patient in the state of septic shock, using an anti-soluble CD127 antibody;

obtaining a reference value, wherein the reference value is:

the level of expression of soluble CD127 measured in a biological sample taken from a patient when the patient was in a state of septic shock, using an anti-soluble CD127 antibody; or the mean value of levels of expression of soluble CD127 measured in a pool of biological samples taken from patients when the patients were in a state of septic shock, using an anti-soluble CD127 antibody;

wherein the levels of expression of soluble CD127 in the test sample and in the biological sample, or the pool of biological samples, used to obtain the reference value, are measured within 2 days, or within 1 day, after the septic shock, or 4 days, 3 days, 2 days, or 1 day after the septic shock; and wherein the risk of mortality in the patient in the state of septic shock is indicated when the level of expression of soluble CD127 in the test sample is greater than the level of expression of soluble CD127 in the reference value.

2. The method according to claim 1, wherein the measurement of the expression of soluble CD127 is combined with estimating at least one severity score selected from the group consisting of a Sequential Organ Failure Assessment and a Simplified Acute Physiology Score II, in order to evaluate the risk of mortality for said patient.

3. The method according to claim 1, wherein the anti-soluble CD127 antibody is a monoclonal anti-soluble CD127 antibody.

* * * * *